US012773296B2

(12) United States Patent
Erhardt et al.

(10) Patent No.: US 12,773,296 B2
(45) Date of Patent: Oct. 27, 2026

(54) IMPLANTABLE ARRAY WITH A REFERENCE STRUCTURE AND METHOD OF MANUFACTURING THE SAME

(71) Applicant: CorTec GmbH, Freiburg (DE)

(72) Inventors: Johannes Erhardt, Bad Bellingen (DE); Martin Schuettler, Emmendingen (DE); Thomas Stieglitz, Freiburg (DE); Michael Bock, Heidelberg (DE)

(73) Assignee: CorTec GmbH, Freiburg (DE)

( * ) Notice: Subject to any disclaimer, the term of this patent is extended or adjusted under 35 U.S.C. 154(b) by 204 days.

(21) Appl. No.: 17/844,324

(22) Filed: Jun. 20, 2022

(65) Prior Publication Data

US 2022/0313108 A1 Oct. 6, 2022

Related U.S. Application Data

(63) Continuation of application No. PCT/EP2020/086881, filed on Dec. 17, 2020.

(30) Foreign Application Priority Data

Dec. 19, 2019 (EP) .................................... 19218170

(51) Int. Cl.
*A61B 90/00* (2016.01)
*A61B 5/00* (2006.01)
(Continued)

(52) U.S. Cl.
CPC .............. *A61B 90/39* (2016.02); *A61B 5/293* (2021.01); *A61B 5/4094* (2013.01); (Continued)

(58) Field of Classification Search
CPC ....... A61B 90/39; A61B 5/293; A61B 5/4094; A61B 2090/3954; A61B 2562/046; (Continued)

(56) References Cited

U.S. PATENT DOCUMENTS

2009/0171184 A1* 7/2009 Jenkins .................. A61B 34/10 606/130
2015/0297316 A1* 10/2015 Grinstaff ................ A61B 90/39 600/431
(Continued)

FOREIGN PATENT DOCUMENTS

CN 107735017 A 2/2018
CN 110267704 A 9/2019

OTHER PUBLICATIONS

Salam, M. et al. 2014. Subdural porous and notched mini-grid electrodes for wireless intracranial electroencephalographic recordings. Journal of Multidisciplinary Healthcare, 2014:7, 573-586 (Year: 2014).*

(Continued)

*Primary Examiner* — Anhtuan T Nguyen
*Assistant Examiner* — Dean N Edun
(74) *Attorney, Agent, or Firm* — Myers Wolin, LLC

(57) ABSTRACT

An implantable array, such as an electrode array, is provided. The array is suitable for being placed in anatomic tissue of a human or animal body, and has a structure for referencing predefined distinct points of the implantable electrode array in magnetic resonance images. A structure is arranged in a predefined portion of the implantable array, where the structure has multiple patterns, each pattern having a predefined form and formed from a material having a magnetic susceptibility which is different from the magnetic susceptibility of the anatomic tissue surrounding the implantable array when placed in the human or animal body. Each pattern is in a predefined spatial relationship with one of the predefined distinct points.

6 Claims, 3 Drawing Sheets

(51) Int. Cl.
*A61B 5/293* (2021.01)
*H05K 3/28* (2006.01)

(52) U.S. Cl.
CPC . *A61B 2090/3954* (2016.02); *A61B 2562/046* (2013.01); *A61B 2562/125* (2013.01); *H05K 3/288* (2013.01)

(58) Field of Classification Search
CPC .............. A61B 2562/125; A61B 5/291; A61B 2560/0406; A61B 2560/0468; A61B 2562/08; A61B 2562/164; A61B 5/064; A61B 5/062; H05K 3/288
See application file for complete search history.

(56) References Cited

U.S. PATENT DOCUMENTS

| | | | | |
|---|---|---|---|---|
| 2016/0120457 | A1 | 5/2016 | Wu et al. | |
| 2018/0369572 | A1* | 12/2018 | Schouenborg ....... | A61N 1/0551 |

OTHER PUBLICATIONS

Erhardt, JB Et al. 2017. Precise Localization of Silicone-based Intercranial Planar Electrodes in Magnetic Resonance Imaging. 2017 39th Annual International Conference of the IEEE Engineering in Medicine and Biology Society (EMBC) (Year: 2017).*

Erhardt et al., "Precise Localization of Silicone-based Intercranial Planar Electrodes in Magnetic Resonance Imaging," 39th Annual International Conference of the IEEE Engineering in Medicine and Biology Society, Jul. 11, 2017, pp. 513-516, IEEE.

Yang et al., "Localization of dense intracranial electrode arrays magnetic resonance imaging", NeuroImage, Jun. 30, 2012, pp. 157-165, vol. 63, No. 1, Elsevier Inc., Amsterdam, NL.

International Search Report issued by the European Patent Office for International Patent Application No. PCT/EP2020/086881, mailed Feb. 25, 2021.

The extended European search report with European search opinion issued by the European Patent Office for European Patent Application No. 19218170.9, dated Jul. 2, 2020.

Notice of Review—first Chinese Office Action issued by the Chinese Intellectual Property Office for Chinese Patent Application No. 2020800823036, dated Jun. 6, 2025, with English translation attached.

Search and Claim Report issued by the Chinese Intellectual Property Administration for Chinese Patent Application No. 2020800823036, dated Jun. 2, 2025, with English translation attached.

Communication pursuant to Article 94(3) EPC issued by the European Patent Office for European Patent Application No. 20833851.7, dated Jan. 16, 2025.

J. B. Erhardt, et al., "Precise localization of silicone-based intercranial planar electrodes in magnetic resonance imaging", Jul. 11-15, 2017 39th Annual International Conference of the IEEE Engineering in Medicine and Biology Society, 2017, pp. 513-516 (EMBC), Jeju, South Korea.

* cited by examiner

IMPLANTABLE ARRAY WITH A REFERENCE STRUCTURE AND METHOD OF MANUFACTURING THE SAME

CROSS REFERENCE TO RELATED APPLICATIONS

This application is a continuation of International Application No. PCT/EP2020/086881, filed Dec. 17, 2020, which claims priority to European Patent Application No. 19218170.9, filed Dec. 19, 2019, the contents of each of which are incorporated by reference herein.

FIELD OF THE INVENTION

The present invention relates to an implantable array, in particular to an implantable electrode array, with a reference structure, and to a method of manufacturing an implantable array, in particular an implantable electrode array, with a reference structure which is visible in magnetic resonance images (MRI) when implanted for example in a human or animal body.

BACKGROUND

Such an array is implanted on the surface of the brain e.g., for pre-surgical assessment of cortical electrical activity in patients with epilepsy.

Hereby, MM is used to localize the electrode contacts of the implanted array with respect to the anatomy of the patient. However, metal components or other good electric current conductive materials like carbon and electric conductive polymers may cause MRI artifacts that compromise the results especially in the direct vicinity of the implants. Thin-film implants which may feature 100× less metal thickness may mitigate these artifacts, but thin-film implants produce inconspicuous MM signal voids in many clinical MRI sequences, and are therefore not suitable for localizing the electrode with MM.

On the other hand, implants having very small metal contacts, very thin metal layers, or no metal at all may not become visible in clinical MRI at all.

But imperatively, physicians need to know the implant position, and the value of intracranial EEG increases with the precision of electrode localization.

SUMMARY

The present disclosure is directed towards the problem to provide an implantable array for MRI-based localization of its standard or micro-sized planar electrode contacts, and a method of manufacturing such electrode arrays which can be precisely localized in MRI.

This problem may be solved by the implantable array, in particular by an implantable electrode array, and the method of manufacturing an implantable array, in particular an implantable electrode array, according to the claims.

Accordingly provided is an implantable array, in particular an electrode array, suitable for being placed in anatomic tissue of a human or animal body, comprising

- a structure for referencing predefined distinct points of the implantable electrode array in magnetic resonance images, the structure being arranged in a predefined portion of the implantable array, the structure comprising:
- a plurality of patterns, each pattern having a predefined form and comprising a material having a magnetic susceptibility which is different from the magnetic susceptibility of the anatomic tissue surrounding the electrode array when placed in the human or animal body,
- each pattern being in a predefined spatial relationship with one of the predefined distinct points.

Advantageous embodiments of the invention may comprise the following features. The material may comprise particles with a material selected from the group comprising iron, iron oxide, oxides of rare earths, and pyrolytic carbon material.

The patterns may comprise a material having a magnetic susceptibility which is higher than the magnetic susceptibility of the anatomic tissue surrounding the electrode array when placed in the human or animal body.

Each pattern may be isolated and spaced apart from each other pattern.

The structure may form a grid over the predefined portion of the electrode array.

The predefined points may be at least one of:

electrode contacts, fluidic interfaces, points of geometrical significance.

The predefined form may be a cross-like form.

The predefined portion may comprise at least one of;

a top surface (8), a rear surface, an edge, a corner.

At least three patterns may be aligned along a straight first line, and at least three patterns may be aligned along a straight second line, the second line being perpendicular to the first line.

The material may be polymer, in particular selected from the group comprising silicone rubber, polyurethane, polyimide, epoxy, liquid crystal polymer, and parylene.

The implantable electrode array may comprise at least one layer of a polymer, in particular selected from the group comprising silicone rubber, polyurethane, polyimide, epoxy, liquid crystal polymer, and parylene.

The contacts may form a first grid with a first grid constant, and the patterns may form a second grid with the same grid constant as the metal contacts.

The invention further comprises a method of manufacturing an implantable array suitable for being placed in anatomic tissue of a human or animal body, in particular the electrode array as discussed above, comprising the following steps:

a. A first layer of a polymer is deposited on a mechanical carrier;
b. The first polymer layer is cured;
c. A conductive layer is laminated, or deposited, onto the first polymer layer;
d. The conductive layer is patterned with a laser, thus forming electrode contacts, interconnection tracks and weld pads;
e. A second layer of polymer is deposited;
f. The second layer of polymer is cured;
g. Trenches are cut into the polymer layer using a laser, the trenches defining a MRI reference structure;
h. The trenches are filled with a polymer comprising a material having a magnetic susceptibility which is different from the magnetic susceptibility of the anatomic tissue surrounding the electrode array when placed in the human or animal body;
i. The filling of the trenches is cured;
j. A covering layer of polymer is deposited and cured;

k. Electrical contacts are exposed by removing the covering layer with a laser;

l. The outline of the electrode array is defined by cutting through all deposited layers with a laser;

m. The electrode array is separated from the mechanical carrier.

The polymer may be selected from the group comprising silicone rubber, polyurethane, polyimide, epoxy, liquid crystal polymer, and parylene.

The material may be selected from the group comprising iron, iron oxide, oxides of rare earths, and pyrolytic carbon.

The conductive layer may be selected from the group comprising metal, conductive polymer, carbon.

The material may have a magnetic susceptibility which is higher than the magnetic susceptibility of the anatomic tissue surrounding the electrode array when placed in the human or animal body.

As mentioned above, the implantable array may be an implantable electrode array.

BRIEF DESCRIPTION OF THE DRAWING

The invention and embodiments thereof will be described below in further detail in connection with the drawing.

DETAILED DESCRIPTION OF THE PREFERRED EMBODIMENTS

Figure 1:
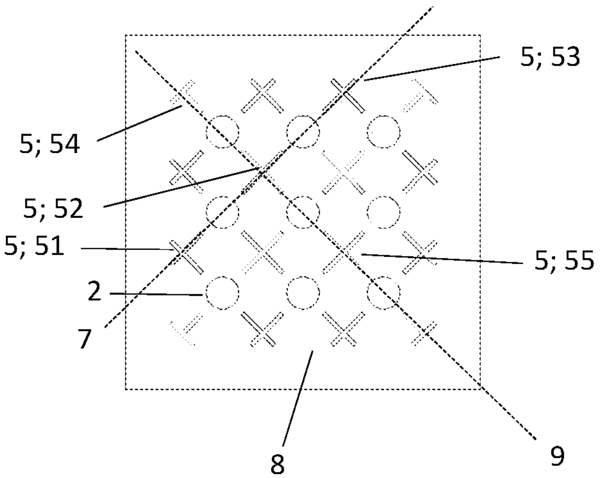
FIG. 1 illustrates the implantable electrode array according to an embodiment of the invention.
Figure 2:
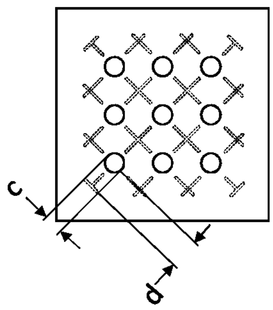
FIG. 2 illustrates distances in the implantable electrode array according to an embodiment of the invention.

FIG. 1 and FIG. 2 illustrate an implantable electrode array according to an embodiment of the invention. The implantable electrode array comprises at least one substrate layer 1 made from a biocompatible polymer. The polymer can be selected from the group comprising silicone rubber, polyurethane, polyimide, epoxy, liquid crystal polymer, and parylene.

The implantable electrode array is flexible such that it can adapt its form to the form of the location in the cortex of a human or animal where it is placed. The electrode array comprises sensor contacts 2 of diameter c on its surface 8. The electrode contacts 2 may be located in apertures 6 in the polymer 1 of a diameter smaller than diameter c.

The electrode array further comprises a structure 5 for referencing predefined distinct points 2, e.g., the contacts 2, of the implantable electrode array in MRI. The structure 5 is arranged on the implantable electrode array, i.e., on the surface 8 or under the surface 8, and comprises single patterns 51, 52, 53.

Each pattern 51, 52, 53 comprises particles (i.e., nanoparticles, NPs) with a material producing a large magnetic susceptibility difference with respect to the surroundings, that is the tissue of the patient where the electrode array is to be placed.

This difference in magnetic susceptibility is linked with a difference in the respective effective transverse relaxation times (T2*), e.g., a very short T2* for the material with a high magnetic susceptibility, and a longer T2* for the surrounding human tissue, having a smaller magnetic susceptibility, such that the MRI signal in and near the pattern is lost, and thus a contrast to the surrounding material is established with the result that the pattern becomes visible in a magnetic resonance image of the electrode array.

The material having a very short T2* for the patterns can be selected from the group comprising, e.g., iron, iron oxide and oxides of rare earths.

The reference structure 5 forms a grid over a predefined portion of the electrode array; each pattern 51, 52, 53, 54, 55 is in a predefined spatial relationship, e.g., distance d, to one of the metal contacts 2 to be referenced.

As can be seen from the figure, each pattern 51, 52, 53, 54, 55 is isolated and spaced apart from each other pattern. The patterns may have cross-like form.

The patterns 51, 52, 53, 54, 55 may be equidistant to each other. At least two patterns 51, 52, 53, 54, 55 may be aligned along a straight first line 7. Moreover, at least two patterns 52, 54, 55 may be aligned along a straight second line 9, the second line 9 being perpendicular to the first line 7. In this example, the patterns form a regular 2-dimensional grid over the surface 8 of the electrode array, as indicated in FIG. 2. However, other forms for the structure 5 are also possible.

As can be seen, the metal contacts form a first grid with a first grid constant, and the patterns form a second grid with the same grid constant as the metal contacts.

Figure 3:
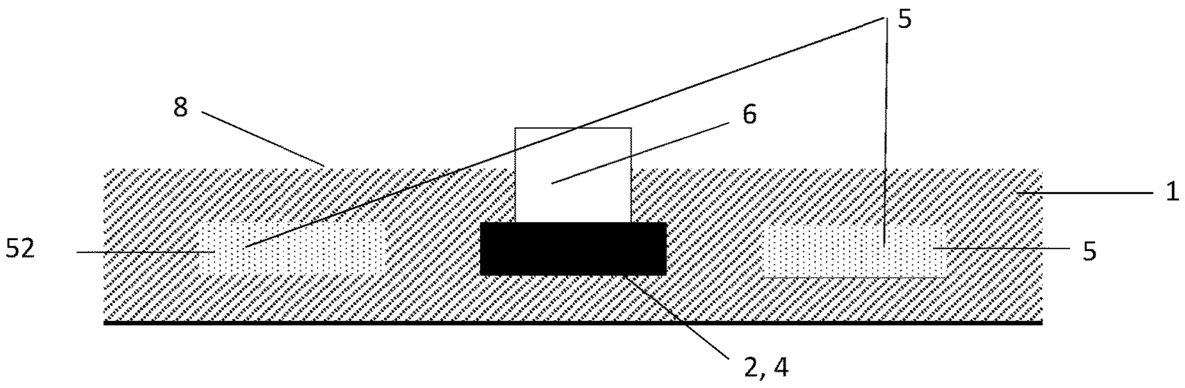
FIG. 3 illustrates sectional view of the implantable electrode array according to an embodiment of the invention.

In sectional view of the implantable electrode array according to FIG. 3, the reference structure 5 is formed under the surface 8 of the substrate 1, i.e., each pattern 51, 52, 53, 54, 55 of the reference structure 5 is surrounded by the substrate 1.

Figure 4:
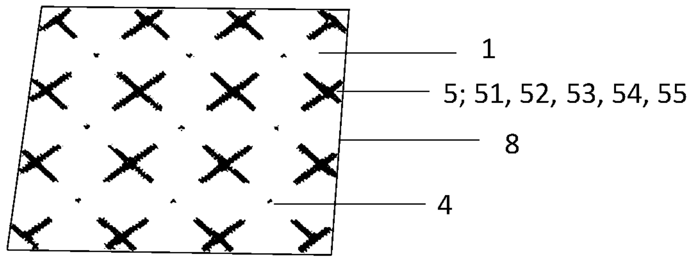
FIG. 4 illustrates the implantable electrode array according to a further embodiment of the invention.

Typical diameters c of the electrode contacts 2 are 4 mm. The apertures 6 may have a diameter of 2.3 mm. Typical electrode arrays may comprise e.g. 3×3 electrode contacts or 3×6 electrode contacts, depending on the intended application. A typical spacing between two electrode contacts 2 (interelectrode spacing) may be 10 mm. Microelectrode arrays, according to a further embodiment of the invention as illustrated in FIG. 4, may have contacts 4 with diameters of about 0.3 mm.

According to a particular variant, the patterns 51, 52, 53, 54, 55 of reference structure 5 may comprise silicone rubber doped with iron oxide (e.g. $Fe_2O_3$) particles. Herein, iron oxide is selected for its good ferromagnetic properties and its very good biocompatibility.

The predefined points 2 which are referenced by the patterns 51, 52, 53, 54, 55 may be a) electrical contacts 2, i.e., sensor contacts; selected from metal, conductive polymer, carbon on the implantable electrode array, b) fluidic interfaces (e.g., inlets or outlets for conveying liquids into the body, or out of the body), c) other points of particular geometrical significance for the physician.

As mentioned above, the structure 5 may form a grid over a predefined portion of the electrode array. The predefined portion may comprise or be at least one of the top surface 8 (i.e., the side where the contacts are), the rear surface (i.e., the side where no contact is), an edge, and a corner of the electrode array, or be in the interior of the electrode array.

Table 1 gives typical, non-limiting dimensions of the implantable electrode arrays with reference structures 5.

TABLE 1

| | | |
|---|---|---|
| Electrode diameter in mm | 0.3 | 4.0 |
| Electrode material | Pt/Ir | MP35N |
| Total sample thickness in mm | 0.29 | 0.27 |
| Reference structure thickness in mm | 0.29 | 0.27 |
| Reference structure design width in mm | 0.50 | 0.50 |

In the following, a manufacturing process of an implantable electrode array with a reference structure 5 is described.

The manufacturing is based on a layer-by-layer deposition method, starting with a mechanical carrier, typically a ceramic substrate: The method comprises the following steps:

a. A layer of preferably some 10 μm to a few 100 μm thick liquid silicone rubber is deposited. The silicone is cured.

b. A metal foil of preferably some μm to a few 10 μm thickness is laminated to the silicone. The metal is patterned with a laser, removing all metal but the electrode contacts, interconnection tracks and weld pads.

c. A second layer of silicone is deposited of preferably some 10 μm to a few 100 μm thickness. The silicone is cured.

d. Trenches are cut into the silicone using a laser. Theses trenches define the shape of the MRI reference structures. The depth of the trenches defined the layer height of the reference structures.

e. The trenches are filled with silicone rubber containing superparamagnetic nanoparticles. The filling of the trenches is cured.

f. A covering layer of silicone rubber of preferably some 10 μm to a few 100 μm is deposited and cured.

g. Metal contacts are exposed by removing silicone with a laser.

h. The outline of the electrode array is defined by cutting through all deposited layers with a laser.

i. The electrode array is separated from the mechanical carrier.

Instead of silicone rubber, any flexible polymer can be used, in particular one from the group comprising silicone rubber, polyurethane, polyimide, epoxy, liquid crystal polymer, and parylene.

The electrode array as described above is particularly well suited for being imaged with MM.

Advantageously, the reference structures as described above can be freely shaped in all dimensions, and the NP concentration can be varied. As a result, the implant thickness could be as little as 50 μm and thus feature high flexibility. Since these reference structures do not alter the outside silicone slab shape, the handling of these implants is identical to that of conventional implants. Due to their distinct contrast to the surroundings, the reference structures may be especially useful for electrode contact placement in sulci. Since the patterns of the reference structure can be placed +on the complete surface of the electrode array like a grid, they can reference the electrode contacts in situ even if the electrode is strongly bent or curved.

What is claimed is:

1. An implantable electrode array suitable for being placed in anatomic tissue of a human or animal body, comprising:

a structure for referencing electrode contacts of the implantable electrode array in magnetic resonance images, the structure being arranged in a predefined portion of the implantable electrode array, the structure comprising:

a plurality of patterns, each pattern having a predefined form and comprising a material having a magnetic susceptibility which is different from the magnetic susceptibility of the anatomic tissue surrounding the array when placed in the human or animal body, each pattern being in a predefined spatial relationship with one of the electrode contacts, wherein the material is a polymer and comprises particles of a material selected from the group consisting of iron, iron oxide, oxides of rare earths, and pyrolytic carbon material, wherein the electrode contacts form a first regular two-dimensional grid with a first grid constant, and the patterns form a second regular two-dimensional grid with a second grid constant identical to the first grid constant, and wherein the structure is arranged at or under a surface of and does not extend beyond the surface of the implantable electrode array.

2. The implantable electrode array of claim 1, wherein the magnetic susceptibility of the material is higher than the magnetic susceptibility of the anatomic tissue surrounding the electrode array when placed in the human or animal body.

3. The implantable electrode array of claim 1, wherein each pattern is isolated and spaced apart from each other pattern.

4. The implantable electrode array of claim 1, wherein the predefined portion comprises at least one of a top surface, a rear surface, an edge, a corner.

5. The implantable electrode array of claim 1, wherein at least three patterns are aligned along a straight first line, and at least three patterns are aligned along a straight second line, the second line being perpendicular to the first line.

6. The implantable electrode array of claim 1, wherein the implantable electrode array comprises at least one layer of a polymer.

* * * * *